(12) United States Patent
Meijer et al.

(10) Patent No.: US 7,232,814 B2
(45) Date of Patent: Jun. 19, 2007

(54) USE OF PAULLONE DERIVATIVES FOR MAKING MEDICINES

(75) Inventors: Laurent Meijer, Roscoff (FR); Conrad Kunick, 48a, Stremelkamp, Hamburg, Allemagne D-21149 (DE)

(73) Assignees: Centre National de la Recherche Scientifique (C.N.R.S.), Paris (FR); Conrad Kunick, Allemagne (DE)

( * ) Notice: Subject to any disclaimer, the term of this patent is extended or adjusted under 35 U.S.C. 154(b) by 470 days.

(21) Appl. No.: 10/203,977

(22) PCT Filed: Feb. 15, 2001

(86) PCT No.: PCT/FR01/00455

§ 371 (c)(1),
(2), (4) Date: Feb. 27, 2003

(87) PCT Pub. No.: WO01/60374

PCT Pub. Date: Aug. 23, 2001

(65) Prior Publication Data

US 2003/0181439 A1    Sep. 25, 2003

(30) Foreign Application Priority Data

Feb. 15, 2000  (FR) ................... 00 01862

(51) Int. Cl.
*A61K 31/55*     (2006.01)
(52) U.S. Cl. ................... 514/212.06; 514/215
(58) Field of Classification Search ........... 514/212.06, 514/215
See application file for complete search history.

(56) References Cited

FOREIGN PATENT DOCUMENTS

| WO | WO 99/21859 | 5/1999 |
|---|---|---|
| WO | WO 99/65910 | 12/1999 |

*Primary Examiner*—San-Ming Hui
(74) *Attorney, Agent, or Firm*—Foley & Lardner LLP (57) ABSTRACT

The invention concerns the use for producing of GSK-3β inhibiting medicines from paullone derivatives. The invention is useful for treating pathologies involving GSK-3β and CDK5.

17 Claims, 7 Drawing Sheets

USE OF PAULLONE DERIVATIVES FOR MAKING MEDICINES

The invention relates to a new use of paullone derivatives in therapeutics.

The paullones constitute a family belonging to the benzazepinones.

The leader of this family, called paullone, corresponds to the following formula:

In the Journal of Medicinal Chemistry, 1999, Vol. 42, No. 15, pages 2909–2919, the authors, one of whom is a co-inventor of the present application, report the inhibitory properties on cyclin-dependent kinases (abbreviated to CDKs) exhibited by paullones, and their antitumour activity in vitro.

The CDKs play a major role notably in regulation of the cell cycle, by controlling transmission between the successive stages of the cell cycle. Their activity is regulated by a great many mechanisms and in particular by binding to cyclins which vary during the cell cycle. Binding to CDK inhibitors leads to deactivation of the CDKs.

Paullone derivatives substituted in various positions, and especially in position 9, have proved to be, as reported in the aforementioned article, strong inhibitors of CDK1/-cyclin B. Thus, 9-nitro-7,12-dihydroindolo[3,2-d] [1]-benzazepin-6 (5H)-one, called alsterpaullone, has an $IC_{50}$ of 0.035 µM and an antitumour activity in vitro an order of magnitude greater than 1 (mean log $IC_{50}$ of the mid-point of the graph=–6.4M).

These inhibitory properties of CDKs, which lead to arrest of the cell cycle, mean that paullone derivatives are of interest for the treatment of pathologies connected with loss of control of proliferation, such as cancers, psoriasis, cardiovascular diseases, infectious diseases, nephrology, neurodegenerative diseases and viral infections.

Surprisingly, the inventors have now demonstrated that some of these paullone derivatives exerted an inhibitory effect on another enzymatic target, namely glycogen synthase kinase-3β or GSK-3β for short, as well as on the CDKs if appropriate, and especially CDK5/p25.

GSK-3β is an essential element of the WNT signal pathway. It is involved in numerous physiological processes: regulation of the cell cycle by controlling levels of cyclin D1 and of β-catenin, dorso-ventral formation during development, action of insulin on glycogen synthesis, axonal excrescence, Tat-mediated HIV-1 neurotoxicity, and others.

Moreover, it is known that GSK-3p and CDK5 are responsible for a good proportion of abnormal hyperphosphorylation of the microtubule-binding tau protein, as observed in the paired helical filaments in Alzheimer's disease and other neurodegenerative "taupathies".

The advantage of having derivatives that are inhibitors of GSK-3β activity for promoting cell division is also being assessed.

The only inhibitors of GSK-3β disclosed to date comprise lithium and certain derivatives of purine.

The selectivity of lithium has not been reported, but in view of the atomic nature of the product it is probable that it should be very low. Moreover, lithium is only active at considerable doses ($IC_{50}$ around 10 mM).

The same applies to the purine derivatives described in application WO 98/16528, which are of low selectivity and have $IC_{50}$ values around 10 µM.

The invention provides a solution to these problems with the use, for manufacturing medicines that are inhibitors of GSK-3β and if appropriate of CDKs, of paullones of high efficacy, having $IC_{50}$ values with respect to GSK-3β of less than 10 µM, and even below 5 µM for a good number of them, and even less than 1 µM. Some of these compounds even have $IC_{50}$ values below 50 nM, even reaching values below 10 nM for some.

In accordance with the invention, for the manufacture of the said medicines with inhibitory effect, notably of GSK-3β, paullone derivatives are used that correspond to general formula (I):

in which

X represents a C=O, C—S—$CH_3$, C—S, or —C—NHOH group;

Z represents C or N;

Y represents, with the adjacent ring, a phenyl or thiazolyl residue;

the ring or rings constituting these derivatives being substituted if appropriate by one or more: halogen atoms, hydroxy, alkylenehydroxy, alkynealkylenehydroxy, alkynehydroxycyclohexyl, alkyl, alkoxy, alkylenealkoxy, alkylenecyano groups, the alkylene group being saturated or unsaturated, the said radicals being straight-chain or branched, of C1 to C18, the said chain being substituted if appropriate by one or more hydroxy or amino groups; one or more trifluoromethyl; —COM; —COOM; or —$CH_2$COOM groups (with M representing a hydrogen atom, a C1 to C18 alkyl group, straight-chain or branched, substituted if necessary by one or more hydroxy and/or amino; nitroso; nitro; or cyano groups;

$R^5$ represents a hydrogen atom or a $C_1$ to $C_5$ alkyl group, $R^{12}$ represents a hydrogen atom, or a —C—$CO_2$—$(CH_3)_3$ group, and the physiologically acceptable salts of these derivatives.

In a preferred family, Y represents, with the adjacent ring, a phenyl residue, and Z=C. This family corresponds to general formula (II):

(II)

in which,

X, $R^5$ and $R^{12}$ are as defined above, and $R^1$ to $R^4$, $R^7$ to $R^{11}$, which may be identical or different, represent a hydrogen atom, a halogen atom (F, Cl, Br, I), a hydroxy, alkylenehydroxy, alkynealkylenehydroxy, alkynehydroxycyclohexyl, alkyl, alkoxy, alkylenealkoxy or alkylenecyano group, these radicals being straight-chain or branched, with C1 to C18, the alkylene group being saturated or unsaturated, the said chain being substituted if necessary with one or more hydroxy or amino groups; a trifluoromethyl group; a —COM, —COOM, or —CH₂COOM group (with M representing a hydrogen atom, a C1 to C18 alkyl group, straight-chain or branched, substituted if appropriate with one or more hydroxy and/or amino groups); a nitroso group; a nitro group; or a cyano group;

and the physiologically acceptable salts of these derivatives.

In another preferred family, Y represents, with the adjacent ring, a thiazolyl residue and Z=C.

This family corresponds to general formula (III):

(III)

in which the substituents have the meanings given above in relation to formula (II).

In yet another family, Y forms, with the adjacent ring, a phenyl group and Z=N. This family corresponds to formula (IV):

(IV)

in which the substituents have the meanings given in relation to formula (II).

A group of preferred paullone derivatives in these various families corresponds to the case where X represents C=O.

In another group X represents C—S—CH₃ or C—S.

In yet another group X represents —C—NHOH.

In general, the derivatives of the invention advantageously have an $IC_{50}$ with respect to GSK-3β below 10 μM and for many of them below 1 μM, $IC_{50}$ values below 100 nM and even below 10 nM being obtainable.

Particularly preferred paullones of these groups belong to the families of formula (II) or formula (III) with $R^9$ selected from —NO₂, —CN, —Cl, —Br, —CF₃, C1–C5 alkyl, in particular methyl, or a hydrogen atom, $R^2$ and/or $R^3$ selected from alkoxy (of $C_1$ to $C_3$ for the alkyl radical), and especially methoxy, alkylenecyano, vinylalkoxy, or propylene, the other substituents being hydrogen.

The invention relates in particular to the use, for manufacturing medicines that are selectively inhibitors of GSK-3β, of CDK1 and of CDK5, of paullone derivatives of formula (II) in which X=CO, $R^9$ is selected from —NO₂, —CN, —Br, —Cl, —CF₃, H, and $R^2$ and/or $R^3$ represent H, $C_1$–$C_5$ alkoxy, especially methoxy, alkylenecyano, especially methylenecyano, the other substituents being hydrogen.

The invention relates quite particularly to the use of paullones of formula (II) in which X=CO, $R^9$ represents —NO₂, —CN, —Br, —Cl or —CF₃, the other substituents representing hydrogen.

The invention relates again quite particularly to the use of paullones of formula (II) in which X=CO, $R^9$ represents the meanings given above and $R^2$ and $R^3$ both represent a $C_1$ to $C_5$ alkoxy group, in particular methoxy, or $R^2$ represents an alkylenecyano group, in particular ethylenecyano.

The invention also relates in particular to the use, for manufacturing medicines that are selectively inhibitors of GSK-3β, of paullones of general formula (II) in which X=SCH₃ and $R^9$ is as defined above and represents in particular a halogen atom, in particular bromine.

According to another embodiment of the invention, paullone derivatives of formula (III) in which $R^9$ is as defined above in its preferred meanings, the other substituents representing a hydrogen atom, are used for the manufacture of medicines that are inhibitors of GSK-3β, CDK1 and CDK5, with a greater selectivity with respect to GSK-3β and CDK1.

It is to be noted that 9-cyano-2,3-dimethoxypaullone is a novel product and falls within the scope of the invention on this basis.

The invention therefore makes it possible to produce medicines having the selectivity required for a given application.

The medicines manufactured in accordance with the invention using the said paullone derivatives are quite particularly suitable for the treatment of pathologies in which GSK-3β is involved.

This applies in particular to endocrinology, for example in the case of diabetes, where GSK-3β inhibitors can be used as insulin-mimetics. It will be recalled that insulin acts by a cascade of biochemical events leading to inhibition of GSK-3β and that this inhibition is responsible for the cells' response to insulin.

These medicines are also of considerable interest for the treatment of neurodegenerative diseases, such as Alzheimer's disease. Hyperphosphorylation of tau protein caused by CDK5 and GSK-3β can in fact be inhibited by paullone derivatives. By administering the drugs made according to the invention, it is then possible, owing to their inhibitory effect both on CDK5 and GSK-3β, to prevent hyperphosphorylation of tau protein in Alzheimer's patients and combat neurodegeneration and ischaemia.

These drugs are also of considerable interest for treating manic-depressive illnesses.

We may also mention their use for the treatment of cancers, where their inhibitory effect both on GSK-3β and CDK1/2/5, which translates into apoptosis of the tumour cell, is utilized advantageously.

These drugs also prove effective for the treatment of diseases caused by single-celled parasites such as malaria, the trypanosomes, leishmanias, toxoplasmas, pneumocystis etc., or for multicellular parasites, such as fungi and parasitic worms. The genomes of these parasites in fact contain GSK3 homologous genes, but they are different from human GSK-3.

They can also be used in the cardiovascular sphere for treating or preventing, in particular, atherosclerosis, recurrence of stenosis or angiogenesis, by altering the equilibrium between proliferation and apoptosis, and by controlling the levels of β-catenin.

They will also be used advantageously for the treatment of infectious diseases, such as AIDS.

During development of the medicines, the active principles, used in therapeutically effective quantities, are mixed with vehicles that are pharmaceutically acceptable for the chosen route of administration.

Thus, for oral administration, the medicines are prepared in the form of gelatin capsules, tablets, lozenges, capsules, pills, drops and the like. Such medicines can contain from 1 to 100 mg of active ingredient per unit.

For administration by injection (intravenous, subcutaneous, intramuscular), the medicines are in the form of sterile or sterilizable solutions. They may also be supplied in the form of suspensions or emulsions. The doses per dosage unit can vary from 1 to 50 mg of active ingredient. The daily dosage is chosen so as to obtain a final concentration of at most 100 μM of paullone derivative in the blood of the treated patient.

As a guide, the dosage that can be used in man corresponds to the following doses: thus, in one or more doses of 10 to 50 mg/day, for example, are administered to the patient for the treatment of tumours or of parasitoses.

In oder to illustrate the invention, without however limiting its scope, other characteristics and advantages are described in the examples given below.

In these examples, reference will be made to FIGS. 1 to 6, showing respectively.

Characterization of the Paullones

Elementary analyses were carried out using a PerkinElmer 2400 instrument for elementary analysis of CHN. The $^1H$ NMR spectra were recorded at 400 MHz and the $^{13}C$ NMR spectra at 100 MHz on a Bruker AMX 400 instrument, with tetramethylsilane as internal reference.

The syntheses of the compounds in Table 2 were carried out by the methods described in J. of Medicinal Chemistry mentioned above. The synthesis of 2-iodopaullone, 2-bromo-9-nitropaullone, 2,3-dimethoxy-9-nitropaullone, 9-cyano-2,3-dimethoxypaullone, 7-bromo-5-(4-nitrophenylhydrazono)-4,5-dihydro-1-H-[1]benzazepin-2(3H)-one, 7,8-dimethoxy-5-(4-nitrophenylhydrazono)-4,5-dihydro-1H-[1]benzazepin-2(3H)-one, is described in Examples 1 to 6.

Buffers

The buffers used have the following compositions:

Homogenization buffer: 60 mM of β-glycerophosphate, 15 mM of p-nitrophenylphosphate, 25 mM of Mops (pH 7.2), 15 mM of EGTA, 15 mM of $MgCl_2$, 1 mM of DTT, 1 mM sodium vanadate, 1 mM of NaF, 1 mM of phenylphosphate, 10 μg of leupeptin/ml, 10 μg of aprotinin/ml, 10 μg of soya trypsin inhibitor/ml and 100 μM of benzamidine.

Buffer A: 10 mM of $MgCl_2$, 1 mM of EGTA, 1 mM of DTT, 25 mM of Tris-HCl pH 7.5, 50 μg of heparin/ml.

Buffer C: homogenization buffer, but containing 5 mM of EGTA, and without NaF and protease inhibitors.

Tris-saline buffer of Tween-20 (TBST): 50 mM of Tris pH 7.4, 150 mM of NaCl, 0.1% of Tween-20".

Hypotonic lysis buffer (HLB): 50 mM of Tris-HCl pH 7.4, 120 mM of NaCl, 10% of glycerol, 1% of Nonidet-P40, 5 nM of DTT, 1 mM of EGTA, 20 mM of NaF, 1 mM of orthovanadate, 5 μM of microcystine, 100 μg/ml of each of the following products: leupeptin, aprotinin, pepstatin.

Preparations of Kinases and Determinations of the Activities

The activities of the kinases were determined in buffer A or C (unless stated otherwise), at 30° C., at a final ATP concentration of 15 μM. The values of the blank tests were subtracted and the activities were calculated in pmol of phosphate incorporated for an incubation time of 10 minutes. The values of the activities are generally expressed as a percentage of the maximum activity, i.e. in the absence of inhibitors.

Control tests were carried out using appropriate dilutions of $Me_2SO$. In some cases, as pointed out later, phosphorylation of the substrates is determined by autoradiography after SDS-PAGE.

The GSK-3β used is either the enzyme purified from rabbit muscle or expressed and purified from Sf9 insect cells (Hughes et al., 1992, Eur. J. Biochem., 203: 305, 311). The determinations were carried out with a dilution to 1/100 in 1 mg of BSA/ml of DTT 10 mM, with 5 µl of GS-1 40 µM as substrate, in buffer A, in the presence of 15 µM [γ$^{32}$P] ATP (3000 Ci/mol; 1 mCi/ml) in a final volume of 30 µl. After incubation for 30 minutes at 30° C., 25 µl aliquots of supernatant were applied to strips of Whatman P81 phosphocellulose paper, 2.5×3 cm, and 20 seconds later the filters were washed 5 times (for at least 5 minutes each time) in a solution of 10 ml of phosphoric acid/liter of water. The wet filters underwent counting in the presence of 1 ml of ACS scintillation fluid (Amersham).

The CDK1/cyclin B used was extracted using a homogenization buffer from starfish oocytes (*Marthasterias glacialis*) and purified by affinity chromatography on beads of p9$^{CKShs1}$-Sepharose, from which the product was eluted with free p9$^{CKShs1}$, as described by Meijer et al., 1997 (Methods in Enzymology, Vol. 283: 113–128), and Borgne et al., 1999, J. Biol. Chem. 274: 11977–11986.

Kinase activity was determined in buffer C, with 1 mg of histone H1/ml, in the presence of 15 µM of [γ$^{32}$P] ATP (3000 Ci/mmol; 1 mCi/ml) in a final volume of 30 µl.

After incubation for 10 minutes at 30° C., 25 µl aliquots of supernatant were deposited on P81 phosphocellulose papers and treated as described above.

The CDK5/p35 was reconstituted by mixing equal quantities of recombinant mammalian CDK5 and of p35 expressed in *E. coli* in the form of GST (glutathione-S-transferase) fusion protein and purified by affinity chromatography on glutathione-agarose. The enzyme activity of the complex was determined in buffer C as described for CDK1/cyclin B.

Phosphorylation of tau in vitro and in vivo

The phosphorylation of tau in vitro was carried out using purified GSK-3β and human recombinant tau-32 protein as substrate. After incubation for 30 minutes in the presence of various concentrations of alsterpaullone, in the conditions of investigation of GSK-3β described above, reaction of the kinase was stopped by adding Laemmli buffer. The tau protein was resolved in SDS-PAGE at 10% and its degree of phosphorylation was visualized by autoradiography.

Cells and viruses: the Sf9 cells (InVitrogen, San Diego, Calif.) were cultivated at 27° C. in a Grace monolayer culture medium (Gibco BRL, Gaithersburg, Md.), supplemented with 10% of fetal calf serum and 50 µg of gentamycin/ml and 2.5 µg of amphotericin/ml. BaculoGold was obtained from PharMingen (San Diego, Calif.), and pVL1392 from InVitrogen.

Transfection of tau: the shortest human tau isoform, with XbaI and BamHI, was excised from a pNG2 bacterial expression vector (Biernat et al., 1993, Neuron, 11: 153–163) and the gene coding for htau23. The gene was inserted in the baculovirus transfer vector pVL1392 cut with the same endonucleases. The BaculoGold system was used for constructing the vector containing the tau baculovirus. The DNA of BaculoGold is a modified type of baculovirus containing a lethal deletion.

Co-transfection of the DNA of BaculoGold with a complement baculovirus transfer vector makes it possible to recover the lethal deletion from this viral DNA and reconstitute viable virus particles carrying the sequence coding for htau23.

The plasmid DNA used for the transfections was purified using QIAGEN cartridges (Hilden, Germany).

The Sf9 cells cultivated in monolayers (2×10$^6$ cells in a 60 mm cell culture vessel) were co-transfected with baculovirus DNA (0.5 µg of BaculoGold DNA) and with the pVL1392 derivatives (2 µg) using the method of calcium phosphate co-precipitation. The infected cells were examined for presence of recombinant protein 5 days post-infection by SDS-PAGE and Western blot.

Treatment of Sf9 Cells with Kinase Inhibitors

To determine the effects of inhibitors of aminopurvalanol and alsterpaullone on the phosphorylation of tau, the Sf9 cells infected with the baculovirus expressing htau23 were treated 36 hours after infection (when the cells have already expressed levels of tau sufficient for the development of cellular processes) with 20 µM of inhibitors for 3 hours before being harvested.

Western Blot of tau:

The Sf9 cells were infected with a recombinant virus at MOI of 1 to 5.

The cell lysates were prepared in the hypotonic lysis buffer (HLB).

After centrifugation for 15 minutes at 16000 g, the supernatant was recovered and its NaCl concentration was increased to 500 mM. The supernatant was then boiled for 10 minutes and recentrifuged at 16000 g for 15 minutes. The proteins (3 µg) were resolved by SDS-PAGE, transferred to a PVDF membrane and investigated by Western blot with the following antibodies: AT-8 (1:2000), AT-180 (1:1000), AT-100 (1:500), PHF-1 (1:600) and K9JA anti-tau polyclonal antibody. Immunostaining was visualized using an ECL chemiluminescence system (Amersham, Braunschweig, Germany).

Inhibition in Situ of CDK5 in the Striatum

Striatum slices from adult mouse brain are prepared in accordance with the standard methodology. Monitoring equilibrium in a Krebs bicarbonate buffer oxygenated with continuous aeration (95% $O_2$/5% $CO_2$), the slices are treated with various concentrations of alsterpaullone, or with 10 µM of roscovitin for 60 minutes, or they are left in the Krebs bicarbonate buffer for the same length of time. The slices are homogenized by sonication in 1% of SDS at boiling and 50 mM of NaF. The concentrations of proteins are determined by the BCA method using a standard BSA curve. Equal quantities of proteins (80 µg) were subjected to SDS-PAGE using 15% acrylamide gel, transferred by electrophoresis on a nitrocellulose membrane and subjected to immunoblot with a specific phosphorylation antibody that selectively detects DARPP-32 phosphorylated on Thr75.

EXAMPLE 1

2-Iodo-7,12-dihydro-indolo[3,2-d][1]benzazepin-(5H)-one(2-iodopaullone)

A mixture of phenylhydrazine (162 mg, 1.5 mmol) and 7-iodo-1H-[1]benzazepin-2,5-(3H, 4H)-dione (301 mg, 1 mmol) in glacial acetic acid (10 mL) is stirred for 1 hour at 70° C. Concentrated sulphuric acid (0.1 mL) is added and stirring is continued for 1 hour at 70° C. After cooling to room temperature, the mixture is poured into an aqueous solution of sodium acetate at 5%. The precipitate is removed by filtration, washed with water and crystallized from ethanol. 57%6 of beige crystals are obtained, m.p. 303° C. (decomp.); IR (KBr): 3270 (NH), 1640 (C=O); $^1$H-NMR (DMSO-$d_6$, 400 MHz): δ (ppm) 3.52 (s, 2H, $CH_2$), 7.04–7.10 (3, 2H), 7.19 ("t", 7.6 Hz, 1H), 7.43 (d, 8.2 Hz, 1H), 7.66–7.69 (m, 2H), 8.07 (d, 1.5 Hz, 1H), 10.17 (s, 1H, lactam NH), 11.66 (s, 1H, indole NH); $C_{16}H_{11}N_2O$ (374.18); Calc. C, 51.4, H, 3.0, N, 7.5; Found C, 51.0, H, 3.3, N, 7.2.

EXAMPLE 2

2-Bromo-7,12-dihydro-9-nitro-indolo[3,2-d][1]benzazepin-6(5H)-one(2-bromo-9-nitropaullone)

7-Bromo-5-(4-nitrophenylhydrazono)-4,5-dihydro-1H-[1]benzazepin-2(3H)-one (389 mg, 1 mmol) is refluxed in diphenyl ether (20 mL) for 2 hours under nitrogen. After cooling to room temperature, hexane (50 mL) is added. The precipitate is filtered, washed with hexane and crystallized from ethanol/toluene. Deep yellow crystals are obtained (35%), m.p. >330° C.; IR (KBr): 3310 (NH), 1670 (C=O); $^1$H-NMR (DMSO-$d_6$, 400 MHz): δ (ppm)=3.69 (s, 2H, $CH_2$), 7.23 (d, 1H, 8.6 Hz), 7.59–7.64 (m, 2H), 7.96 (d, 1H, 2.0 Hz), 8.09 (dd, 1H, 9.1/2.0 Hz), 8.77 (d, 1H, 1.5 Hz), 10.32 (s, 1H, lactam NH), 12.46 (s, 1H, indole NH); $C_{16}H_{10}BrN_3O_3$ (372.19; Calc. C, 51.6, H, 2.7, N, 11.2, Br, 21.5; found C, 51.5, H, 3.0, N, 10.8, Br, 21.3.

EXAMPLE 3

2,3-Dimethoxy-7,12-dihydro-9-nitro-indolo[3,2-d][1]benzazepin-6(5H)-one(2,3-dimethoxy-9-nitropaullone)

7,8-Dimethoxy-5-(4-nitrophenylhydrazono)-4,5-dihydro-1H-[1]benzazepin-2(3H)-one (370 mg, 1 mmol) is refluxed in diphenyl ether (20 mL) for 2 hours under nitrogen. After cooling to room temperature, hexane is added (50 mL). The precipitate is filtered, washed with hexane and crystallized from ethanol/toluene. Deep yellow crystals are obtained (63%), m.p. >330° C.; IR (KBr): 3340 (NH), 1660 (C=O); $^1$H-NMR (DMSO-$d_6$, 400 MHz): δ (ppm)=3.58 (s, 2H, $CH_2$), 3.81 (s, 3H, $OCH_3$), 3.88 (s, 3H, $OCH_3$), 6.90 (s, 1H), 7.31 (s, 1H), 7.31 (s, 1H), 7.59 (d, 1H, 9.2 Hz), 8.05 (dd, 1H, 8.9/2.3 Hz), 8.69 (d, 1H, 2.0 Hz), 9.94 (s, 1H, lactam NH), 12.32 (s, 1H, indole NH); $C_{18}H_{15}N_3O_5$ (353.35); Calc. C, 61.2, H, 4.3, N, 11.9; found C, 60.9, H, 4.4, N, 11.8.

EXAMPLE 4

2,3-Dimethoxy-6-oxo-5,6,7,12-tetrahydro-indolo[3,2-d][1]benzazepin-9-carbonitrile(9-cyano-2,3-dimethoxypaullone)

9-Bromo-2,3-dimethoxy-7,12-dihydro-indolo[3,2-d][1]benzazepin-6(5H)-one(387 mg, 1 mmol) and copper(I) cyanide (179 mg, 2 mmol) are refluxed for 2 hours in N-methyl-2-pyrrolidone (10 mL). After cooling to room temperature, water (10 mL) is added and the reaction mixture is stirred for 15 minutes. The precipitate is removed by filtration and stirred for a further 15 minutes in a mixture of water (10 mL) and ethylenediamine (2.5 mL). The precipitate is eliminated by filtration, washed with a 10% aqueous cyanide solution and crystallized from ethanol/toluene. Colourless crystals (40%) are obtained, m.p. >330° C.; IR (KBr): 3300/3200 (NH), 2220 (CN), 1660 (C=O); $^1$H-NMR (DMSO-$d_6$, 400 MHz): δ (ppm)=3.53 (s, 2H, $CH_2$), 3.80 (s, 3H, $OCH_3$), 3.87 (s, 3H, $OCH_3$), 6.89 (s, 1H), 7.29 (s, 1H), 7.49 (s, 1H), 7.49 (dd, 1H, 8.6/1.5 Hz), 7.58 (d, 1H, 8.2 Hz), 8.27 (s, 1H), 9.89 (s, 1H, lactam NH), 12.10 (s, 1H, indole NH); $C_{19}H_{15}N_3O_3$ (333.36); Calc. C, 68.5, H, 4.5, N, 12.6; found C, 68.0, H, 4.6, N, 12.0.

EXAMPLE 5

7-Bromo-5-(4-nitrophenylhydrazono)-4,5-dihydro-1-H-[1]benzazepin-2(3H)-one

7-Bromo-1H-[1]benzazepin-2,5(3H, 4H)dione (254 mg, 1 mmol) (Kunick C. (1991), Arch. Pharm. (Weinheim) 324, 579–581), 4-nitrophenylhydrazine hydrochloride (284 mg, 1.5 mmol) and sodium acetate (123 mg, 1.5, mmol) are stirred in glacial acetic acid (10 ml) for 1 hour at 70° C.

After cooling to room temperature, the mixture is poured into a 5% aqueous solution of sodium acetate (20 ml). The precipitate is recovered by filtration, washed with water, and crystallized from ethanol. Yellow crystals are obtained, with a yield of 52%.; m.p. 300° C. (decomp.); IR (KBr)/3220 (NH), 1670 (C=O); $^1$H-NMR (DMSO-$d_6$, 400 MHz):

−δ (ppm)=2.56–2.59 and 3.02–3.06 (m, AA'XX', 4H, CH$_2$—CH$_2$), 6.99 (d, 1H, 8.1 Hz), 7.33 (d, 2H, 9.2 Hz), 7.56 (dd, 1H, 8.7/2.6 Hz), 7.75 (d, 1H, 2.0 Hz), 8.16 (d, 2H, 9.6 Hz), 7.56 (dd, 1H, 8.7/2.6 Hz), 7.75 (d, 1H, 2.0 Hz), 8.16 (d, 2H, 9.6 Hz), 9.87 (s, 1H, NH), 10.19 (s, 1H, NH); C$_{16}$H$_{15}$BrN$_4$O$_3$ (389.22); Calc. C, 49.4, H, 3.4, N, 14.4, Br, 20.5; Found C, 49.1, H, 3.4, N, 14.1, Br, 20.2.

EXAMPLE 6

7,8-Dimethoxy-5-(4-nitrophenylhydrazono)-4,5-dihydro-1H-[1]benzazepin-2(3H)-one 7,8-Dimethoxy-1H-[1]benzazapin-2,5[3H, 4H)dione (235 mg, 1 mmol) (Schultz C. et al., (1999) J. Med. Chem., 42, 2909–2919), 4-nitrophenylhydrazine hydrochloride (569 mg, 3 mmol) and sodium acetate (246 mg, 3 mmol) are stirred in glacial acetic acid (10 ml) for 1 hour at 70° C.

After cooling to room temperature, the mixture is poured into a 5% aqueous solution of sodium acetate (20 ml). The precipitate is recovered by filtration, washed with water, and crystallized from ethanol. Yellow crystals are obtained, with a yield of 60%; m.p. 286° C. (decomp.); IR (KBr)/3260/3180 (NH), 1680 (C=O); $^1$H-NMR (DMSO-d$_6$, 400 MHz):
−δ (ppm)=2.53–2.56 and 2.99–3.03 (m, AA'XX', 4H, CH$_2$—CH$_2$), 3.77 (s, 3H, OCH$_3$), 3.81 (s, 3H, OCH$_3$), 6.65 (s, 1H), 7.20 (s, 1H), 7.32 (d, 2H, 9.2 Hz), 8.13 (d, 2H, 9.2 Hz), 9.53 (s, 1H, NH), 10.06 (s, 1H, NH); C$_{38}$H$_{18}$N$_4$O$_5$ (370.38); calc. C, 58.4, H, 4.9, N, 15.1; found C, 57.8, H, 4.9, N, 14.8.

EXAMPLE 7

Investigation of the Inhibition of GSK-3β, of CDK5/p35 and of CDK1/Cyclin B by the Paullones Alsterpaullone The activity of alsterpaullone was studied on several highly purified kinases.

The kinase activities were determined with a suitable substrate (GSK-3β: GS1 peptide; CDKs: histone Hi) in the presence of 15 μM of ATP and at increasing concentrations of alsterpaullone and kenpaullone.

The activity is expressed as a percentage of the maximum activity.

Figure 1:
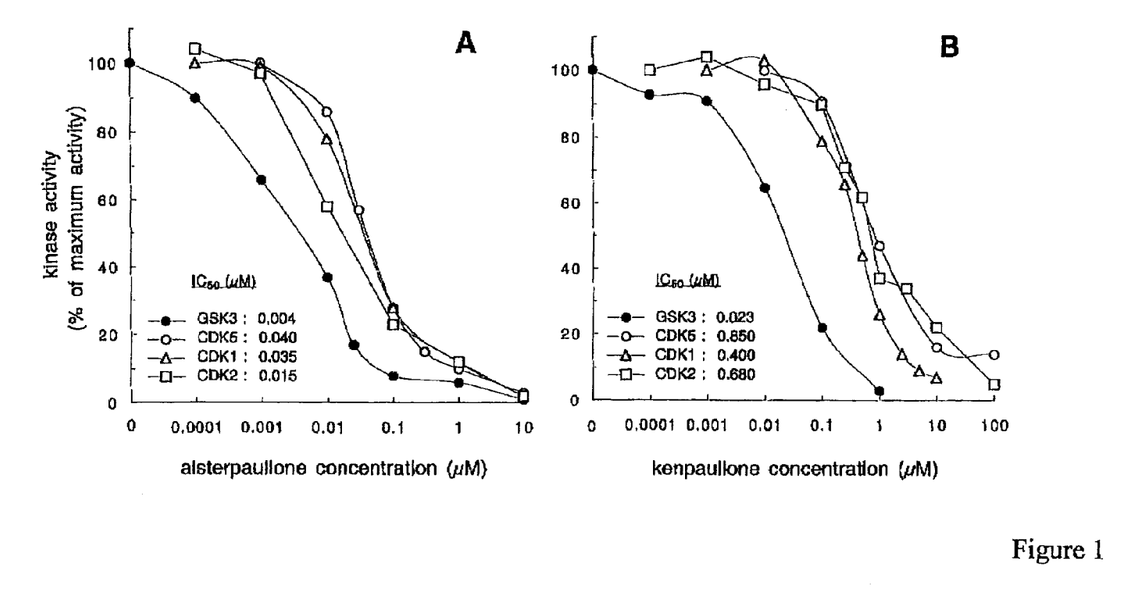
FIGS. 1A and 1B, inhibitory activity with respect to CDKs, CDK1/CDK2, and GSK-3, of alsterpaullone (FIG. 1A) and of kenpaullone (FIG. 1B) as a function of the concentration of these paullones, FIG. 2, the formulae of paullones according to the invention, FIGS. 3A to 3C, the $IC_{50}$ values of paullones according to the invention with respect to one of the protein kinases GSK3, CDK1/cyclin B, CDK5/p25 as a function of their $IC_{50}$ values with respect to the other 2 protein kinases, FIG. 4, the curves showing the inhibition of GSK-3p by alsterpaullone for competition with ATP, FIGS. 5A and 5B, the inhibitory effect of alsterpaullone on phosphorylation of tau by GSK-3β in vitro and in vivo, and FIG. 6, inhibition of the phosphorylation of DARPP-32 by CDK5 on Thr75 in vivo by alsterpaullone.

The results obtained are shown in FIG. 1 and Table 1. The IC$_{50}$ values were calculated from the dose/response curves and are expressed in μM.

TABLE 1

| Enzyme | Alsterpaullone IC50 (μM) |
|---|---|
| CDK 1/cyclin B |  |
| CDK 2/cyclin A |  |
| CDK 2/cyclin E | 0.200 |
| CDK 4/cyclin D1 | >10.000 |
| CDK 5/p35 |  |
| GSK-3 α | 0.004 |
| GSK-3 β | 0.004 |
| erk 1 | 22.000 |
| erk 2 | 4.500 |
| c-raf | >10.000 |
| MAPKK | >100.000 |
| c-jun N-terminal kinase | >10.000 |
| protein kinase C α | >100.000 |
| protein kinase C β1 | >100.000 |
| protein kinase C β2 | >100.000 |
| protein kinase C γ | >100.000 |
| protein kinase C δ | >100.000 |
| protein kinase C ε | >100.000 |
| protein kinase C η | >100.000 |
| protein kinase C ζ | >100.000 |
| cAMP-dependent protein kinase | 7.000 |
| cGMP-dependent protein kinase | >100.000 |
| casein kinase 1 | >100.000 |
| casein kinase 2 | >100.000 |
| Insulin receptor tyrosine kinase | >100.000 |

(<0.01 μM (■), 0.01–0.1 μM (▨), 0.1–1 μM (▨), 1–10 μM (□) > 10 μM (□))

It can be seen that most of the kinases tested are slightly inhibited or not at all (IC$_{50}$>10 μM).

It will be noted that as well as the effect on CDK1/cyclin B, alsterpaullone inhibits CDK2/cyclin A, CDK2/cyclin E, CDK5/p25 and GSK-3α/GSK-3β (IC$_{50}$ respectively 15, 200, 40 and 4 nM).

Other Paullones According to Formula I

Figure 2:
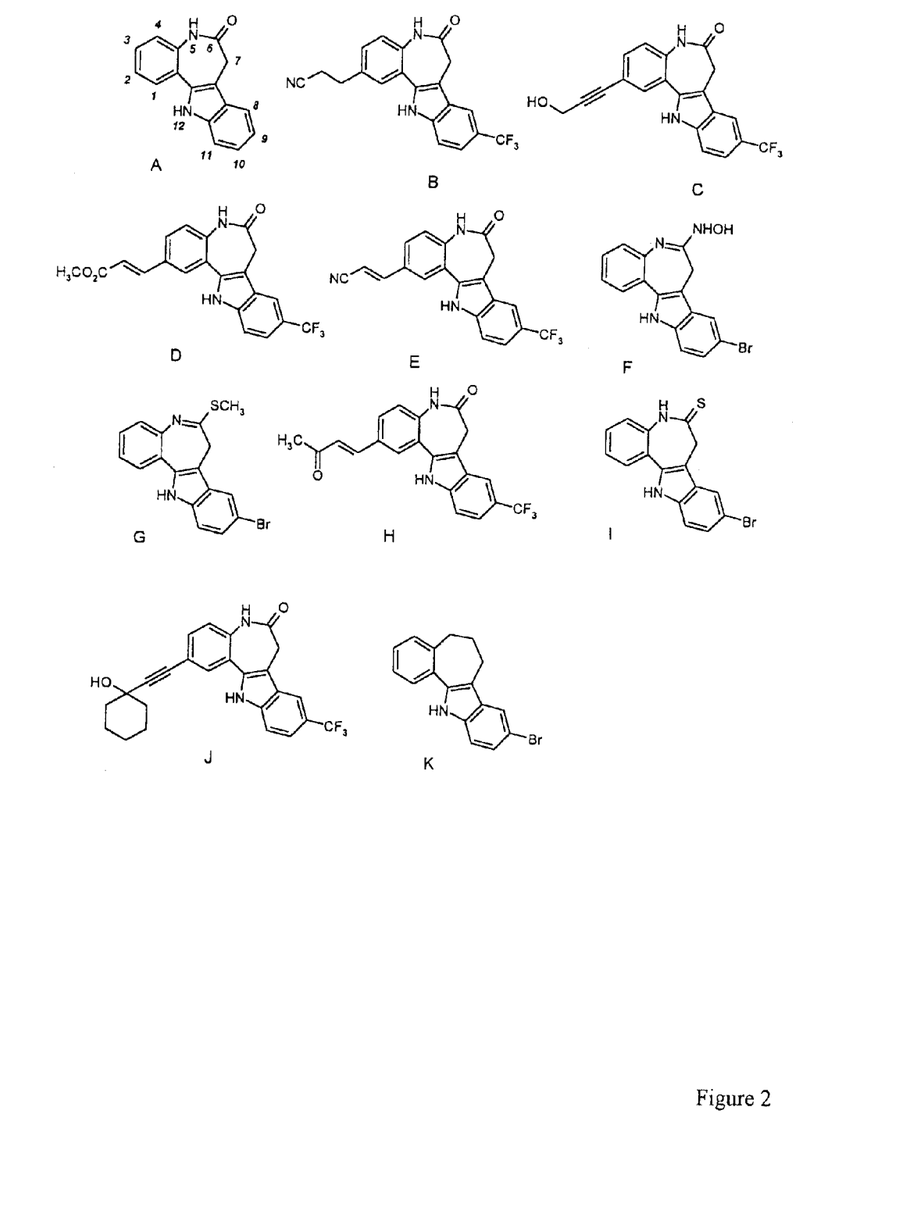

Tables 2A and 2B given below and FIG. 2 show the inhibitory effect of paullones used according to the invention with respect to GSK-3β, CDK5/p25 and CDK1/cyclin B.

TABLE 2A

| Number | Compounds | GSK3 | CDK1 | CDK5 |
|---|---|---|---|---|
| 98 N 215 | alsterpaullone (9-Nitropaullone) | 0.004[d] | 0.035[b] | 0.040[b] |
| 98 N 210 | 9-cyanopaullone | 0.010[b] | 0.024[b] | 0.044[b] |
| 98 N 356 | 2,3-dimethoxy-9-nitropaullone | 0.013[b] | 0.024[b] | 0.021[b] |
| 98 N 217 | 9-cyano-2,3-dimethoxypaullone | 0.018[b] | 0.044[b] | 0.060[b] |

TABLE 2A-continued

| Number | Compounds | GSK3 | CDK1 | CDK5 |
|---|---|---|---|---|
| 96 N 619 | kenpaullone (9-Bromopaullone) | 0.023[b] | 0.400[c] | 0.350[c] |
| 97 N 343 | 9-chloropaullone | 0.024[b] | 0.600[c] | 0.300[c] |
| 97 N 487 | 9-trifluoromethylpaullone | 0.030[b] | 0.400[c] | 0.500[c] |
| 98 N 357 | 3-(6-oxo-9-trifluoromethyl-5,6,7,12-tetrahydro-indolo[2-3-d] [1]benzazepin-2-yl)-propionitrile (B) | 0.033[b] | 0.047[b] | 0.033[b] |
| 98 N 002 | 2,3-dimethoxy-9-trifluoromethylpaullone | 0.075[b] | 0.280[c] | 0.430[c] |
| 98 N 048 | 9-bromo-12-methyloxycarbonylmethylpaullone | 0.075[b] | 1.400[d] | 350.000[c] |
| 97 N 353 | 9-fluoropaullone | 0.080[b] | 1.600[d] | 1.300[d] |
| 97 N 608 | 9-bromo-2,3-dimethoxypaullone | 0.100[c] | 0.200[c] | 0.500[c] |
| 97 N 483 | 9-bromo-2,3-dimethoxypaullone | 0.120[c] | 3.000[d] | 8.000[d] |
| 97 N 352 | 9-methylpaullone | 0.130[c] | 2.000[d] | 6.300[d] |
| 97 N 345 | 10-bromopaullone | 0.140[c] | 1.300[d] | 2.700[d] |
| 97 N 318 | 2-bromopaullone | 0.200[c] | 3.300[d] | 5.000[d] |
| 97 N 344 | 11-chloropaullone | 0.200[c] | 1.400[d] | 2.900[d] |
| 98 N 351 | 2-(3-hydroxy-l-propinyl)-9-trifluoromethylpaullone (C) | 0.200[c] | 0.300[b] | 2.000[d] |
| 98 N 354 | 2-bromo-9-nitropaullone | 0.200[c] | 0.053[b] | 0.120[c] |
| 98 N 259 | 2-iodopaullone | 0.250[c] | 3.700[d] | 7.400[d] |
| 98 N 051 | 9-bromo-12-(2-hydroxyethyl)-paullone | 0.300[c] | 3.000[d] | 140.000[c] |
| 98 N 211 | 9-bromo-12-methylpaullone | 0.400[c] | 6.200[d] | 400.000[c] |
| 98 N 350 | (E)-3-(6-oxo-9-trifluoromethyl-5,6,7,12-tetrahydro-indolo[2-3-d] [1]benzazepin-2-yl)-acrylonitrile (E) | 0.400[c] | 0.270[c] | 9.500[d] |
| 97 N 486 | 9-bromo-5-(methyloxycarbonylmethyl)paullone | 0.500[c] | 6.400[d] | 5.300[d] |
| 98 N 223 | 11-methylpaullone | 0.500[c] | 3.000[d] | 9.000[d] |
| 97 N 317 | paullone (A) | 0.620[c] | 7.000[d] | 10.100[c] |
| 98 N 225 | 11-ethylpaullone | 0.700[c] | 3.800[d] | 23.000[c] |
| 98 N 216 | 9-bromo-7,12-dihydro-6-(hydroxyamino)-indolo[2-3-d] [1] benzazepine (F) | 0.750[c] | 1.000[d] | 2.100[d] |
| 97 N 609 | 2,9-dibromopaullone | 0.800[c] | 0.300[c] | 10.000[c] |
| 97 N 347 | 11-bromopaullone | 0.900[c] | 1.300[d] | 1.400[d] |
| 97 N 485 | 2,3-dimethoxypaullone | 0.900[c] | 4.300[d] | 5.400[d] |
| 98 N 262 | (E)-3-(6-oxo-9-trifluoromethyl-5,6,7,12-tetrahydro-indolo[2-3-d] [1]benzazepin-2-yl)-acrylic acid methyl ester (D) | 0.900[c] | 4.300[d] | 130.000[c] |
| 97 N 610 | 9-bromo-7,12-dihydro-6-methylthio-indolo[2-3-d] [1]benzazepine (G) | 1.200[d] | 43.000[c] | 450.000[c] |
| 98 N 358 | (E)-2-(3-oxo-1-butenyl)-9-trifluoromethylpaullone (H) | 1.400[d] | 0.320[c] | 34.000[c] |
| 98 N 213 | 9-bromo-12-ethylpaullone | 1.500[d] | 23.000[c] | 260.000[c] |
| 97 N 612 | 9-bromo-7,12-dihydro-indolo[2-3-d] [1]benzazepine-6 (5H)-thione (I) | 2.000[d] | 2.300[d] | 8.000[d] |
| 98 N 047 | 2-bromo-9-trifluoromethylpaullone | 2.000[d] | 0.240[c] | 3.000[d] |
| 98 N 349 | 2-[2-(1-hydroxycyclohexyl)-ethinyl]-9-trifluoromethyl-paullone (J) | 2.000[d] | 3.200[c] | 8.300[d] |
| 97 N 613 | 9-bromo-5-methylpaullone | 2.100[d] | 20.000[c] | 130.000[c] |
| 97 N 351 | 9-methoxypaullone | 2.200[d] | 0.900[c] | 2.100[d] |
| 98 N 236 | 2-iodo-9-trifluoromethylpaullone | 2.200[d] | 0.700[c] | 7.000[d] |
| 98 N 046 | 9-bromo-12-(tert.-butyloxycarbonyl)-paullone | 2.300[d] | 70.000[c] | 800.000[c] |
| 98 N 212 | 9-bromo-12-(2-propenyl)-paullone | 4.000[d] | 60.000[c] | 240.000[c] |
| 97 N 482 | 9-bromo-4-hydroxypaullone | 4.300[d] | 40.000[c] | 850.000[c] |
| 98 N 049 | 8,10-dichloropaullone | 5.000[d] | 2.500[d] | 350.000[c] |
| 98 N 001 | 5-benzyl-9-bromopaullone | 10.000[c] | 35.000[c] | 270.000[c] |
| 97 N 607 | 9-bromo-4-methoxypaullone | 16.000[c] | 250.000[c] | 400.000[c] |
| 98 N 224 | 9-bromo-5-ethylpaullone | 24.000[c] | 470.000[c] | 300.000[c] |
| 98 N 209 | 9-bromo-5,7-bis-(tert.-butyloxycarbonyl)-paullone | 130.000[c] | 80.000[c] | >1000[c] |
| 97 N 484 | 4-methoxypaullone | 140.000[c] | 430.000[c] | 100.000[c] |
| 98 N 347 | 9-bromo-5,6,7,12-tetrahydro-benzo[6-7]cyclohept[1,2,b] indole (K) | 180.000[c] | 51.000[c] | 860.000[c] |
| 98 N 214 | 2-phenyl-4-(2-thienyl)-5H-pyrido[2-3-d] [1] benzazepine-6(7H)-thione (L) | 350.000[c] | 33.000[c] | 700.000[c] |
| 98 N 208 | 9-bromo-5,7,12-tri-(tert.-butyloxycarbonyl)-paullone | 500.000[c] | 150.000[c] | 1000.000[c] |
| 97 N 611 | 9-bromo-5,12-bis-(tert.-butyloxycarbonyl)-paullone | 640.000[c] | 1000.000[c] | >1000[c] |
| 98 N 220 | 4-(4-chlorophenyl)-2-(2-naphthyl)-5H-pyrido[2-3-d] [1]benzazepine-6(7H)-thione (M) | >1000[c] | >1000[c] | >1000[c] |
| 98 N 348 | 5,6,7,12-tetrahydro-benzo[6-7]cyclohept[1,2-b]indole (N) | >1000[c] | 130.000[c] | >1000[c] |

[a] <0.01 μM:
[b] 0.01–0.1 μM:
[c] 0.1–1 μM
[d] 1–10 μM
[e] 10 μM

Table 2B also shows the $IC_{50}$ values for GSK3, CDK1 and CDK5 for other paullone derivatives used according to the invention. The meanings represented by the substituents are shown, for each compound, when it is not a hydrogen atom.

TABLE 2B

| Compounds | GSK3 | CDK1 | CDK5 |
|---|---|---|---|
| X = —SCH3; $R^9$ = —Br | 0.034 | 43.000 | 160.000 |
| Y = thienyl residue; $R^9$ = —Br | 0.120 | 0.600 | 4.000 |
| $R^2$ = —CH=CH—CO—$CH_3$; $R^9$ = —$CF_3$ | 0.350 | 4.300 | 15.000 |
| $R^9$ = $R^{11}$ = —F | 0.400 | 3.400 | 10.000 |
| Y = thienyl; $R^9$ = —Cl | 0.400 | 0.500 | 5.000 |
| Y = thienyl; $R^9$ = —$CH_3$ | 1.300 | 4.000 | 40.000 |
| $R^2$ = $R^3$ = —OH | 2.200 | 32.000 | 42.000 |
| $R^2$ = —I; $R^9$ = —Br | 4.200 | 0.320 | 30.000 |
| Z = pyridyl | 5.500 | 2.200 | 3.300 |

Figure 3:
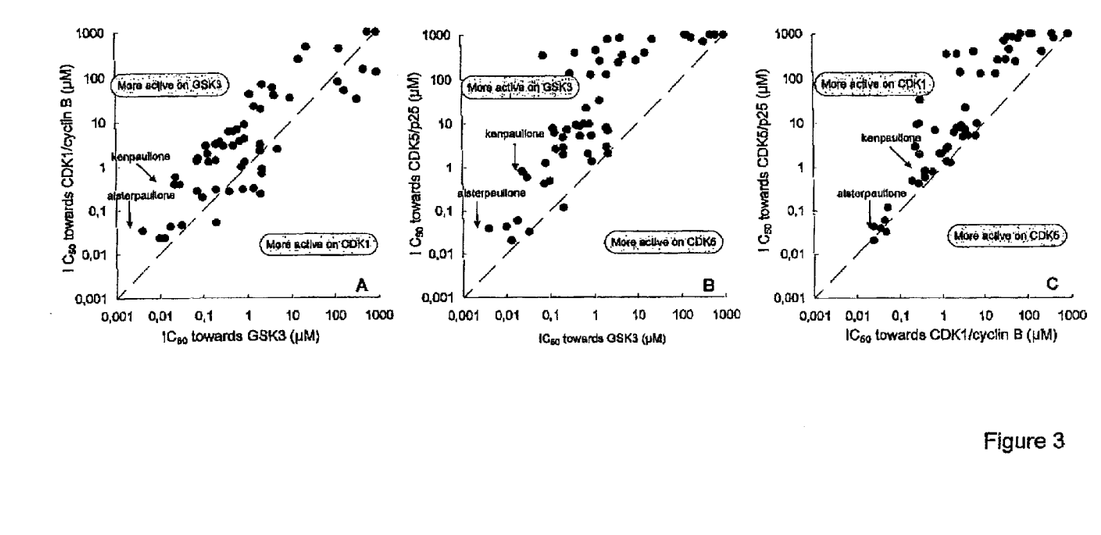

For comparing the effects of the active compounds on GSK-3β and the CDKs, FIGS. 3A to 3C show the $IC_{50}$ values with respect to each enzyme (CDK1/cyclin B, CDK5/p25 and GSK-3β) as a function of the $IC_{50}$ values with respect to two other kinases.

This analysis shows that the efficacies of the paullones with respect to CDK1 and CDK5 are closely related, but are less so with respect to GSK-3p and the CDKs.

EXAMPLE 8

Study of the Inhibition of GSK-3β by the Paullones in Competition with ATP

Figure 4:
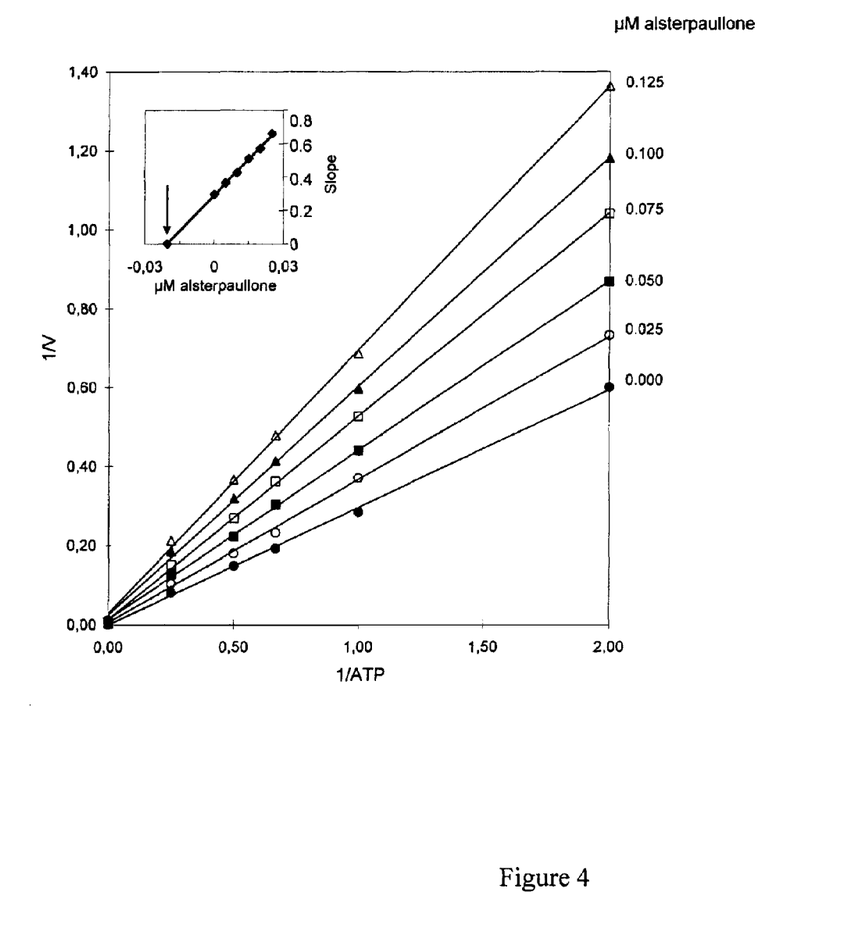

FIG. 4 presents kinetic data from determination of the activity of GSK-3β at different concentrations of alsterpaullone. The enzyme activities are determined as described above. FIG. 4A: primary curve 1/V versus 1/ATP. The ATP concentrations in this reaction mixture vary from 0.5 to 4 μM. The concentration of GS-1 is kept constant at 4 μM. The inset shows the gradients as a function of the concentration from the primary curves. The apparent inhibition constant (Ki) is shown by an arrow.

The kinetic experiments demonstrate that alsterpaullone also competes with ATP for binding to GSK-3β.

The apparent inhibition constant (ki) is 20 nM.

EXAMPLE 9

Study of the Inhibition, by Alsterpaullone, of the Phosphorylation of tau in vitro and in vivo by GSK-3β

The inhibitory effect of alsterpaullone on the activity of GSK-3β was determined on a microtubule-binding tau protein. The human recombinant tau protein expressed in bacteria can be phosphorylated in vitro by GSK-3β and this phosphorylation is inhibited in a dose-dependent manner by alsterpaullone with an $IC_{50}$ close to 33 nM.

Figure 5A:
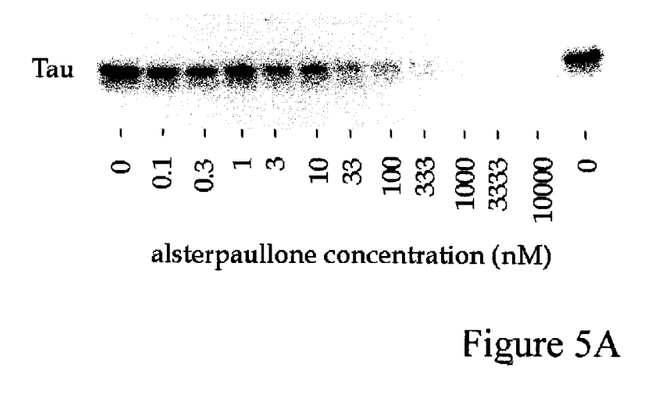
Figure 5B:
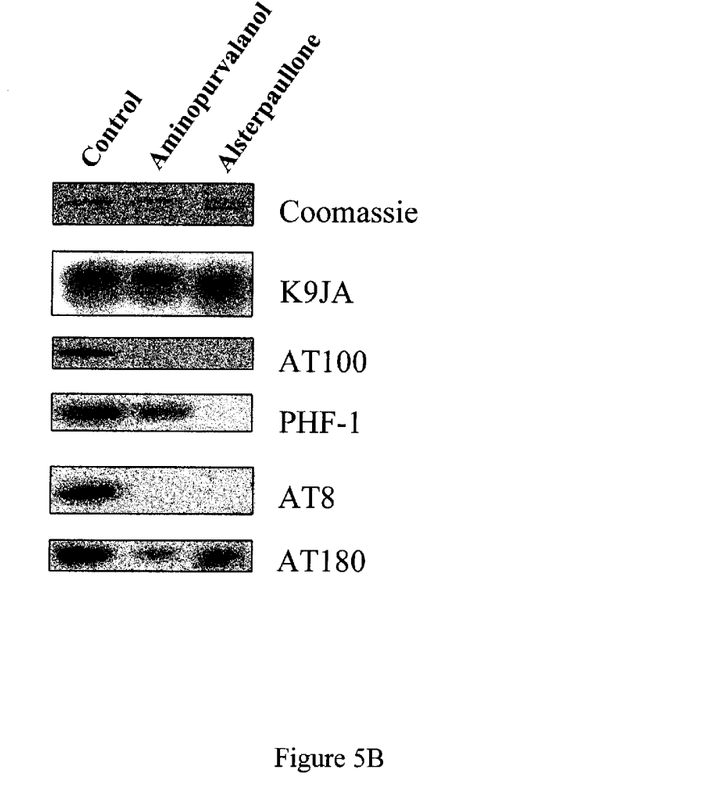
Figure 6:
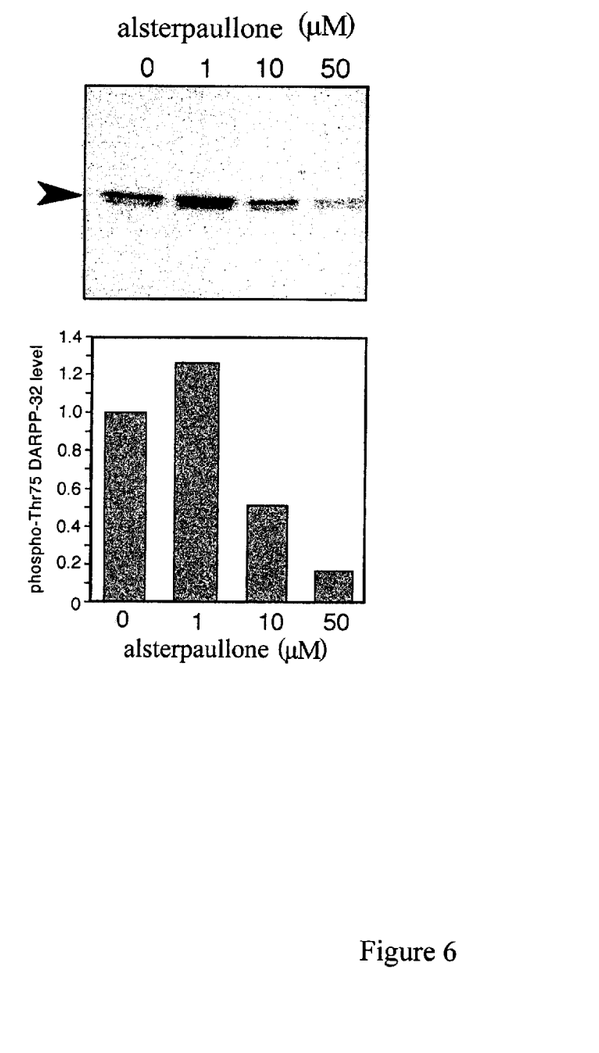

FIG. 5A shows the results of resolution by SDS-PAGE, followed by autoradiography. FIG. 5B gives the results obtained with Sf9 cells expressing htau23 (untreated control), either exposed to alsterpaullone or to aminopurvalanol for 3 hours. The cell lysates (3 μg htau23) are resolved by SDS-PAGE, stained with Coomassie blue or subjected to an immunoblot with different antibodies: K9JA (pantau antibody) which recognizes tau independently of phosphorylation, AT100, which recognizes tau phosphorylated on Thr212 and Ser214, this reaction being very specific to the tau protein of Alzheimer's, PHF-1 (phosphorylated on Ser396/Ser-404, AT8 (phosphorylated on Ser202/Thr205), and AT180 (phosphorylated on Thr231/Ser235).

EXAMPLE 10

Investigation of Inhibition of the Phosphorylation of DARPP-32 by CDKs in vivo

The role of the protein DARPP-32, as a physiological substrate of CDKs/p25, was recently identified by Bibble J. A. et al. (1999), Nature, 402, 669–671. This protein becomes an inhibitor of PKA when it is phosphorylated on Thr75 by CDK5/p25. In vivo, phosphorylation is not observed on this site in p35−/− tissues. To determine the CDK5 inhibiting capacity of alsterpaullone in the brain, slices of striatum (region of the brain expressing DARPP-32) were treated with different concentrations of alsterpaullone. The slices were incubated with 0.1, 10 and 50 μM of alsterpaullone, for 60 minutes. The degree of phosphorylation of DARPP-32 on Thr75 was monitored by Western blot with a phospho-specific antibody and evaluated by quantification of the bands. The results obtained are shown in FIGS. 5A and 5B respectively. It can be seen that alsterpaullone is capable of inhibiting the phosphorylation of DARPP-32 in situ.

EXAMPLE 11

Preparation of a Capsule Using 9-Nitropaullone as Active Ingredient 20 mg of 9-nitropaullone is mixed with the standard excipients used for the manufacture of gelatin capsules.

What is claimed is:

1. A method of treatment of diabetes, comprising administering to a patient in need thereof
   i. an effective amount of a medicine comprising a paullone derivative corresponding to general formula (I):

in which
   X represents a C=O, C—S—$CH_3$, C—S, or —C—NHOH group;
   Z represents C or N;
   Y represents, with the adjacent ring, a phenyl or thiazolyl residue;
   the ring or rings constituting these derivatives being optionally substituted by one or more: halogen atoms, hydroxy, alkylenehydroxy, alkynealkylenehydroxy, alkynehydroxycyclohexyl, alkyl, alkoxy, alkylenealkoxy, alkylenecyano groups, the alkylene group being saturated or unsaturated, these radicals being straight-chain or branched, of C1 to C18, the said chain being optionally substituted with one or more hydroxy or amino groups; one or more trifluorometbyl; —COM; —COOM; or —$CH_2$COOM groups (with M representing a hydrogen atom a C1 to C18 alkyl group, straight-chain or branched, optionally substituted with one or more hydroxy, amino; nitroso; nitro; or cyano groups;

$R^5$ represents a hydrogen atom or a $C_1$ to $C_5$ alkyl group, $R^{12}$ represents a hydrogen atom, or a —C—CO$_2$—(CH$_3$)$_3$ group, and the physiologically acceptable salts of these derivatives, and ii. a pharmaceutically acceptable carrier or vehicle.

2. The method according to claim 1, characterized in that the paullone derivatives correspond to formula (II)

(II)

in which,

X represents a C=O, C—S—CH$_3$, C—S, or —C—NHOH group, $R^5$ represents a hydrogen atom or a $C_1$ to $C_5$ alkyl group and $R^{12}$ represents a hydrogen atom, or a —C—CO$_2$—(CH$_3$)$_3$ group, and $R^1$— to $R^4$, $R^7$ to $R^{11}$, which may be identical or different, represent a hydrogen atom, a halogen atom (F, Cl, Br, I), a hydroxy, alkylenehydroxy, alkynealkylenehydroxy, alkynehydroxycyclohexyl, alkyl, alkoxy, alkylenealkoxy or alkylenecyano group, these radicals being straight-chain or branched, with C1 to C18, the alkylene group being saturated or unsaturated, the said chain being optionally substituted with one or more hydroxy or amino groups; a trifluorometbyl group; a —COM, —COOM, or —CH$_2$COOM group (with M representing a hydrogen atom, a C1 to C18 alkyl group, straight-chain or branched, optionally substituted with one or more hydroxy or amino groups); a nitroso group; a nitro group; or a cyano group;

and the physiologically acceptable salts of these derivatives.

3. The method according to claim 1, characterized in tat the paullone derivatives correspond to formula (III), (III)

in which X represents a C=O, C—S—CH$_3$, C—S, or —C—NHOH group, $R^5$ represents a hydrogen atom or a C1 to C5 alkyl group and $R^{12}$ represents a hydrogen atom, or a —C—CO$_2$—(CH$_3$)$_3$ group, and $R^2$, $R^3$, $R^7$ to $R^{11}$, which may be identical or different, represent a hydrogen atom, a halogen atom (F, Cl, Br, I), a hydroxy, alkylenehydroxy, alkynealkylenehydroxy, alkynehydroxycyclohexyl, alkyl, alkoxy, alkylenealkoxy or alkylenecyano group, these radicals being straight-chain or branched, with C1 to C18, the alkylene group being saturated or unsaturated, the said chain being optionally substituted with one or more hydroxy or amino groups; a trifluorometbyl group; a —COM, —COOM, or —CH$_2$COOM group (with M representing a hydrogen atom, a C1 to C18 alkyl group, straight-chain or branched, optionally substituted with one or more hydroxy or amino groups); a nitroso group; a nitro group; or a cyano group.

4. The method according to claim 1, characterized in that The paullone derivatives correspond to general formula (IV):

(IV)

in which X represents a C=O, C—S—CH$_3$, C—S, or —C—NHOH group, $R^5$ represents a hydrogen atom or a $C_1$ to $C_5$ alkyl group and $R^{12}$ represents a hydrogen atom, or a —C—CO$_2$(CH$_3$)$_3$ group, and $R^1$ to $R^4$, $R^7$ to $R^{11}$, which may be identical or different, represent a hydrogen atom, a halogen atom (F, Cl, Br, I), a hydroxy, alkylenehydroxy, alkynealkylenehydroxy, alkynehydroxycyclohexyl, alkyl, alkoxy, alkylenealkoxy or alkylenecyano group, these radicals being straight-chain or branched, with C1 to C18, the alkylene group being saturated or unsaturated, the said chain being optionally substituted with one or more hydroxy or amino groups; a trifluorometbyl group; a —COM, —COOM, or —CH$_2$COOM group (with M representing a hydrogen atom, a C1 to R18 alkyl group, straight-chain or branched, optionally substituted with one or more hydroxy or amino groups); a nitroso group; a nitro group; or a cyano group.

5. The method according to claim 2, wherein X represents C=O.

6. The method according to claim 2, wherein X represents C—S—CH$_3$, or C—S.

7. The method according to claim 2, wherein X represents —C—NHOH.

8. The method according to claim 2, wherein, $R^9$ is selected from —$NO_2$, —CN, —Cl, —Br, —$CF_3$, C1 to C5 alkyl or a hydrogen atom, $R^2$ and $R^3$ are selected from $C_1$–$C_3$ alkoxy, alkylenecyano, vinylalkoxy, or propylene.

9. The method according to claim 8, wherein X═CO, $R^9$ is selected from —$NO_2$, —CN, —Br, —Cl, —$C_3$, H, and $R^2$ and $R^3$ are independently selected from H, $C_1$–$C_3$ alkoxy, alkylenecyano.

10. The method according to claim 9, characterized in that X═CO, $R^9$ represents —$NO_2$, —CN, —Br, —Cl or —$CF_3$.

11. The method according to claim 9, characterized in that X═CO, $R^9$ represents —$NO_2$, —CN, —Br, —Cl or —$CF_3$, and $R^2$ and $R^3$ both represent a $C_1$ to $C_3$ alkoxy group, or $R^2$ represents an alkylenecyano group.

12. The method according to claim 6, characterized in that $R^9$ is selected from —$NO_2$, —CN, —Br, —Cl, —$CF_3$, H.

13. A method treatment of a disease selected from diabetes and manic-depressive illnesses, comprising administering to a patient in need thereof -nitro-7,12-dihydroindolo [3,2-d] [1]-benzazepin-6(5H)-one.

14. The method according to claim 2, in which X═$SCH_3$ and $R^9$ is selected from —$NO_2$, —CN, —Br, —Cl, —$CF_3$, H.

15. The method according to claim 3, in which $R_9$ is selected from —$NO_2$, —CN, —Br, —Cl, —$CF_3$, H, atom.

16. The method according to claim 1, characterized in that the medicines are prepared for oral administration, in the form of gelatin, tablets, lozenges or capsules.

17. The method according to claim 1, characterized in that the drugs are prepared for administration by injection, in the form of solution.

* * * * *